(12) United States Patent
Huiku

(10) Patent No.: US 7,925,338 B2
(45) Date of Patent: Apr. 12, 2011

(54) DETERMINATION OF THE ANESTHETIC STATE OF A PATIENT

(75) Inventor: Matti Huiku, Espoo (FI)

(73) Assignee: General Electric Company, Schenectady, NY (US)

( * ) Notice: Subject to any disclaimer, the term of this patent is extended or adjusted under 35 U.S.C. 154(b) by 1690 days.

(21) Appl. No.: 11/089,529

(22) Filed: Mar. 24, 2005

(65) Prior Publication Data

US 2006/0217628 A1  Sep. 28, 2006

(51) Int. Cl.
*A61B 5/04* (2006.01)
(52) U.S. Cl. ...................................................... 600/544
(58) Field of Classification Search .................. 600/544, 600/545
See application file for complete search history.

(56) References Cited

U.S. PATENT DOCUMENTS

| 4,828,551 A | 5/1989 | Gertler et al. | |
|---|---|---|---|
| 5,957,885 A | 9/1999 | Bollish et al. | |
| 6,622,036 B1 * | 9/2003 | Suffin | 600/544 |
| 6,631,291 B2 | 10/2003 | Viertiö-Oja et al. | |
| 6,801,803 B2 | 10/2004 | Viertiö-Oja | |
| 2002/0035315 A1 * | 3/2002 | Ali et al. | 600/300 |
| 2002/0173729 A1 * | 11/2002 | Viertio-Oja et al. | 600/544 |
| 2003/0055343 A1 * | 3/2003 | Korhonen | 600/481 |

FOREIGN PATENT DOCUMENTS

| EP | 1 273 265 | 1/2003 |
|---|---|---|
| EP | 1 495 715 | 1/2005 |
| WO | WO-03/094726 | 11/2003 |

OTHER PUBLICATIONS

U.S. Appl. No. 11/089,548, filed Mar. 24, 2005, Huiku.
U.S. Appl. No. 11/089,528, filed Mar. 24, 2005, Takala et al.
*Magnitude of skin vasomotor reflex represents the intensity of nociception under general anesthesia*, Shimoda et al., Journal of the Autonomic Nervous System, Jul. 15, 1998, vol. 71, No. 2-3, Jul. 15, 1998, pp. 183-189 XP002399243, ISSN: 0165-1838 abstract.

* cited by examiner

*Primary Examiner* — Charles A Marmor, II
*Assistant Examiner* — Christian Jang
(74) *Attorney, Agent, or Firm* — Andrus, Sceales, Starke & Sawall, LLP

(57) ABSTRACT

The invention relates to the determination of the anesthetic state of a patient. In order to achieve a mechanism that enables establishment and maintenance of balanced anesthesia, values are established for a set of diagnostic indices. The set includes at least two diagnostic indices of which a first diagnostic index is indicative of the level of hypnosis and a second diagnostic index of the level of nociception in the patient. The combination of the at least two index values obtained is employed for indicating the anesthetic state of the patient. The combination of the at least two index values may further be employed to control the administration of drugs to the patient.

42 Claims, 8 Drawing Sheets

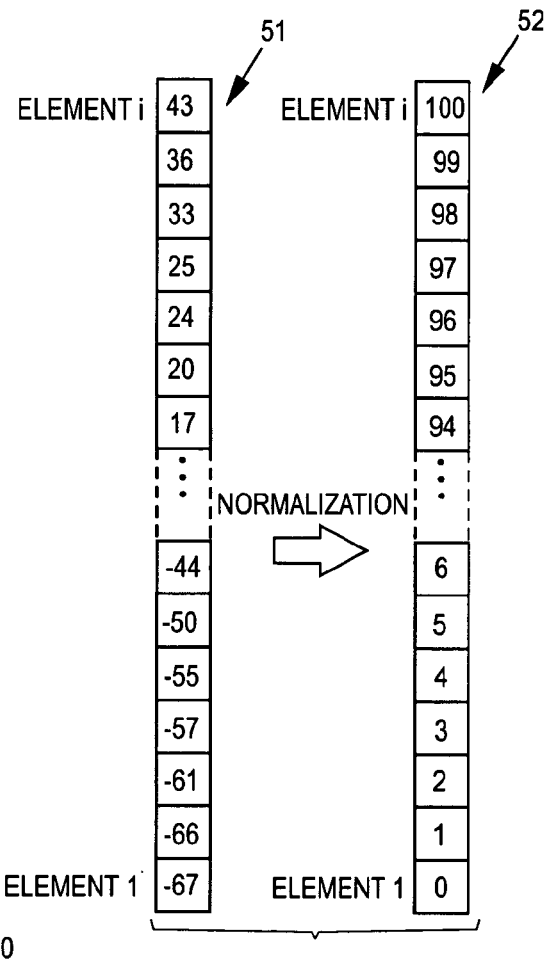
FIG. 5
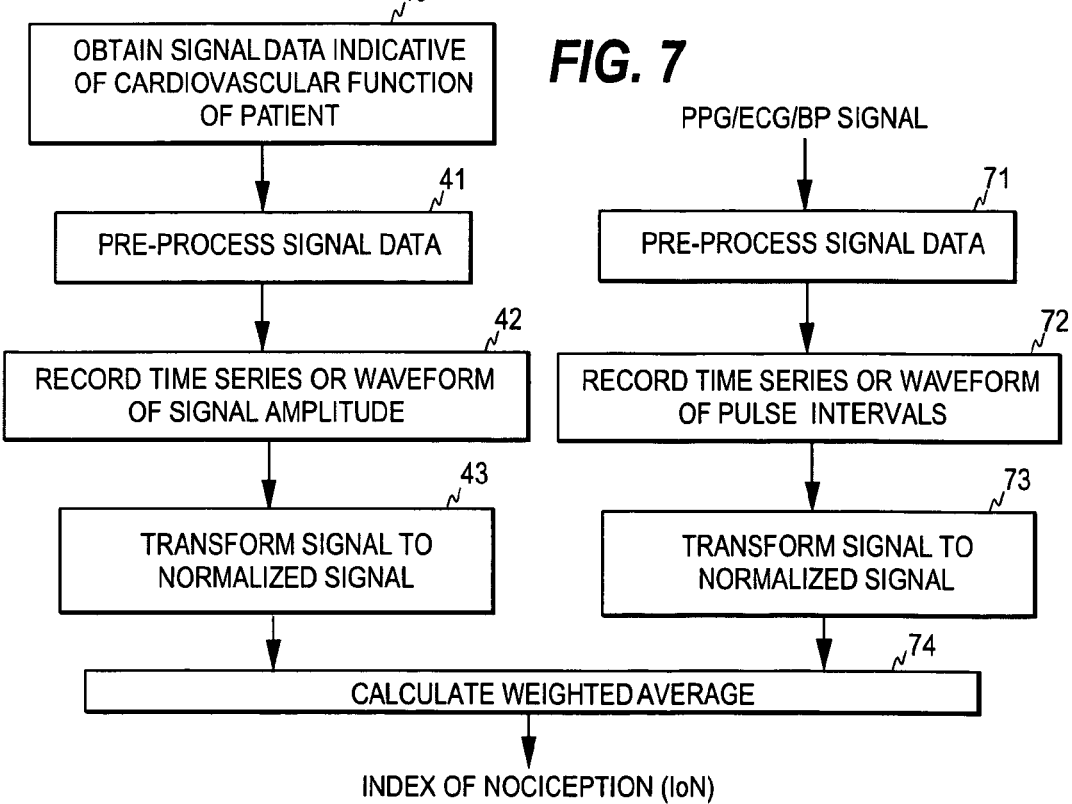

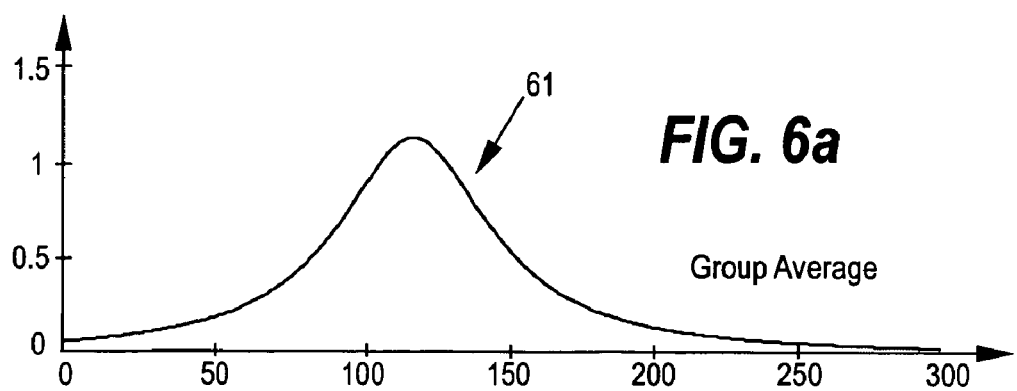
FIG. 6a — Group Average
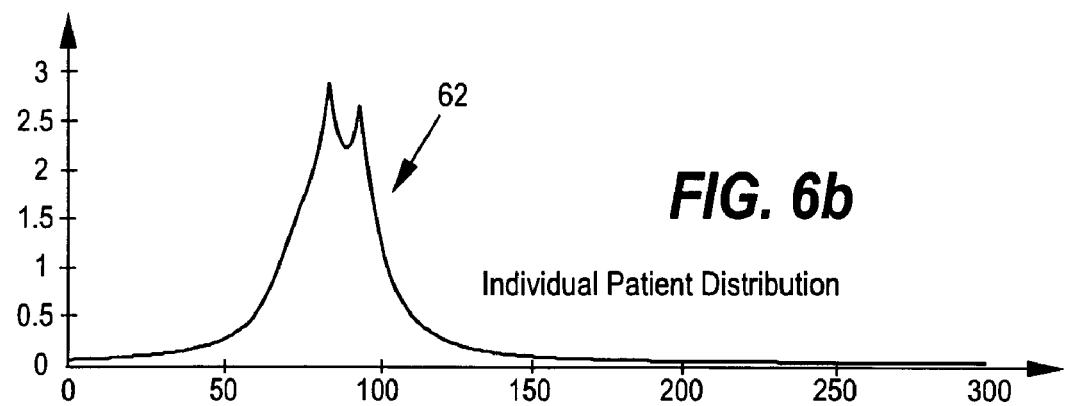
FIG. 6b — Individual Patient Distribution
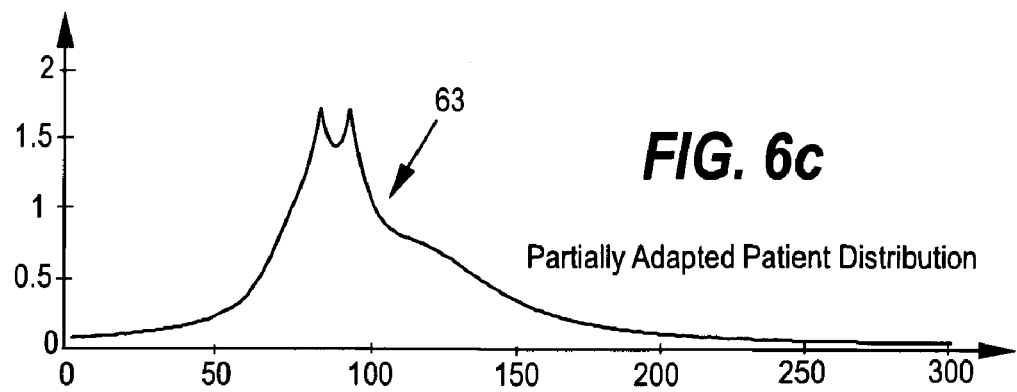
FIG. 6c — Partially Adapted Patient Distribution
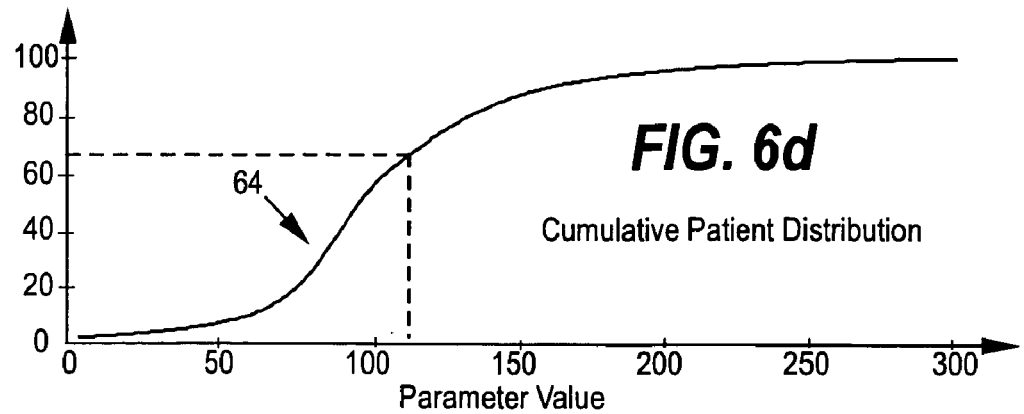
FIG. 6d — Cumulative Patient Distribution
Parameter Value

DETERMINATION OF THE ANESTHETIC STATE OF A PATIENT

FIELD OF THE INVENTION

The present invention relates generally to the determination of the anesthetic state of a patient. The mechanism of the invention may be employed in connection with the administration of anesthetic drugs to a patient, either in a closed loop fashion or as a decision-support tool for an anesthesiologist.

BACKGROUND OF THE INVENTION

A drug delivery system typically consists of a drug delivery unit and a drug dose controller. In this context, the drug delivery unit refers to a mechanical arrangement that delivers drugs to a patient. It may be, for example, a manually or actuator operated syringe, a volume controlled infusion pump, or an evaporator with an anesthesia gas circuit in an anesthesia machine. A drug dose controller in turn refers to a set-up, which may be based on an automated program, an algorithm, or on a decision-making or support tool, which adjusts the dose to a desired level for the patient.

In target controlled infusion (TCI) the operator sets a target concentration of the drug for the patient and an automated controller drives the concentration to the target level by optimally adjusting the infusion rate of a pump. In drug effect monitoring or estimation, a set-up comprising a sensor, a monitor, and a display measures and estimates the effect of a drug in the patient and informs the user about the effect. At present, such estimation or monitoring units are not generally available.

In anesthesia, during which drugs affecting the central nervous system, typically hypnotics and analgesics, are administered, direct measures of drug effects do not exist. However, estimators of the drug effects can be found from physiological or neuro-physiological parameters, which are indirectly indicative of the drug effects in brains. For instance, today the level of consciousness can be reliably estimated based on the EEG measured from the patient. In connection with intra-venous (IV) anesthesia it has also been suggested that the drug concentration in the patient may be estimated by pharmacokinetic (PK) modeling of the drug concentrations in body, from which the effect in brains is predicted using a pharmocodynamic (PD) model. The PK/PD models, which predict drug effects in brains, use certain patient stimulations, such as laryngoscopy, to induce patient responses, and relate the probability of the response to the effect site or plasma drug concentration. The PK/PD model is thus based on the probability of patient response to certain stimulation or certain clinically relevant event, such as loss of consciousness (LOC), in a large patient population.

In operating theatres, a typical drug delivery system is an anesthesia machine or workstation, in which inhaled anesthetic agents are administered using an agent evaporator, i.e. a delivery unit, which is controlled either electronically by a control unit or manually based on measured end-tidal anesthetic agent concentrations and on the concept of Minimum Alveolar Concentration (MAC). The MAC, which is similar to the stimulus-response PK/PD approach, is a statistical measure for the anesthetic agent end tidal concentration at which 50 percent of all patients loose movement response to surgical incision. In present-day intra-venous anesthesia blood plasma or effect site concentrations cannot be continuously measured, which leaves the PK/PD models and clinical observations as the only tools for estimating the drug effects.

Basically, two different control methods are used for the administration of drugs. In an open loop system an anesthesiologist or a physician makes a decision to maintain or change drug concentration based on patient responses, i.e. based on clinically relevant visible effects and a direct or indirect monitoring of vital signs, in particular heart rate and blood pressure. Clinical decisions are often based on certain clinical rules, for instance triggered by a change of blood pressure to a 10 percent higher level than the patient baseline values, or the said decisions are assisted by an automated support system based on similar rules. In a closed loop system, the drug delivery units are automated units, in which a computer program acting as a dose controller controls the drug administration based on measured values of a control variable and the desired set point of the said variable.

In anesthesia and in intensive care units, the drugs delivered by the drug delivery units are typically analgesics, which induce pain relief or antinociception in the patient, hypnotics, which control the depth of sleep or hypnosis, and relaxants, which paralyze the patient. The assessment and control of the level of hypnosis, antinociception, and muscle relaxation constitutes the foundation of modern anesthesia. All typical drugs in anesthesia could be controlled either in an open loop or in a closed loop manner, though commercially validated and approved decision support tools or automated closed loop systems do not exist at present.

There are many basic difficulties in designing a well-performing closed loop system. First, a suitable control variable, which could reliably measure the clinical end effect in the patient, may not be available. Second, due to the complexity of the human body, there is usually not a good single-valued relationship between the pharmaceutical effect site drug concentration and the desired clinical effect. Third, because of the human variability, the pharmaceutical effect site concentration cannot be reliably estimated by the current rather inaccurate general-purpose pharmacokinetic models. Fourth, the design of an accurate, reliable and easy-to-use controller or actuator for the drug delivery is difficult. Fifth, an automated computer program has many interrelated device and patient parameters, which should be known in order to achieve a timely and quantitatively precise delivery of right drugs at right instants and in right doses for each patient.

The design of a fully or partially automated drug delivery system for controlling the muscle relaxation in a patient is, perhaps, the easiest one to achieve. Muscle relaxation is usually achieved by neuromuscular blocking agents (NMBA), which block the neuronal impulse traffic at the muscle-nerve junctions. A complete neuromuscular block paralyzes the patient and thus allows surgery on immobilized body parts.

The level of the neuromuscular block may be measured by monitoring neuromuscular transmission (NMT). This may be done by electrically stimulating a motor nerve, usually the Ulnar nerve of the forearm, and measuring or observing a movement response of the patient hand. Various stimulation modes are available, including a train-of-four (TOF) stimulation in which the fading of the response is measured using four consecutive electric stimuli on the motor nerve. TOF and other neuromuscular blockade estimates are relatively good control parameters for the automated NMBA delivery, as they measure the drug effect (transmission of the neuronal signal to the muscle) in the patient rather directly. The set point of the control parameter value is usually based on a population mean data. NMT may presently be measured continuously in modern anesthesia monitors, such as the Datex-Ohmeda S/5 Anesthesia Monitor. With continuous and reliable NMT measurement a good closed loop control system is thus in principle possible. The neuromuscular blockade may also be measured by using a hand-held stimulator and observing the movement response of the stimulated body part. These devices are suitable for open loop control only.

Hypnosis is an artificially induced altered state of consciousness, which resembles sleep. In anesthesia, the level of hypnosis is controlled by induction of sedative drugs or anesthetic agents. Hypnosis always refers to the suppression or alteration of the (cortical) brain functions. The depth of hypnosis can be clinically tested by non-noxious stimulation of the patient, such as loud speak or light squeeze, shake or touch, and by observing the patient responses, such as eye opening, communication ability, etc. Hypnotic drugs, however, always increase the overall inhibitory neuronal functions, as they usually affect the GABA (gamma-aminobutyric acid) system in the brains. Therefore, the hypnotics suppress both the cortical and subcortical activities in the brains. As a consequence, also the autonomic and reflex functions in the brains are altered and suppressed. This mechanism may be one reason explaining the interaction and the resulting large synergic effect between opioids and hypnotics.

The depth of hypnosis is not directly measurable. Therefore, drug delivery systems have to derive the level of hypnosis from a surrogate signal or from indirectly measured parameters. The most common and popular surrogate signal for this purpose is the EEG (electroencephalogram), from which several parameters, such as the spectral edge frequency (SEF), may be determined. The basic reason for the insufficiency of a single parameter is the variety of drugs and the complexity of the drug effects on the EEG signal in human brains. However, during the past few years, some commercial validated devices for measuring the level of consciousness and/or awareness in clinical set-up during anesthesia or sedation have become available. Two of these devices, which are based on a processed EEG signal but which examine the signal as a whole with its multiple features, have been introduced by Aspect Medical (Bispectral Index) and by Datex-Ohmeda (Entropy Index). Furthermore, a device, an auditory evoked EEG response monitoring device (AAI™) using an active EEG response measurement has been introduced by Danmeter. At present, the situation with the assessment of the level of hypnosis is considered satisfactory, though not fully resolved for such demanding applications as those related to the automated drug delivery. As mentioned above, the hypnotic and analgetic drugs interact and have synergic effects, which call for a multi-parameter input-output drug delivery control. The control of the adequacy of anesthesia is a real challenge, since optimal patient care during surgery or intensive care requires simultaneous adjustment of hypnosis and analgesia.

The assessment and control of the level of analgesia during anesthesia is the least understood component needed for automated drug delivery. Today, no such automated systems exist or no control attempts have been made. Nociception from a damaged tissue site is transmitted to the Central Nervous System (CNS) via several different ascending pathways causing responses that may be cortical pain responses or subcortical stress responses. The stress responses to noxious stimuli may be moderated by the suppression of the pain signal pathways by opioids at the subcortical level, often in the region of the brainstem and spinal cord. In this context, antinociception refers to the blocking or suppression of nociception in the pain pathways at the subcortical level. Both cortical (pain and hypnosis) and subcortical (antinociception) mechanisms play a substantial role in pain management in modern surgical anesthesia and intensive care.

At present, the level of nociception or antinociception or the overall surgical stress cannot be measured. Observations of the blood pressure and heart rate in the patient correlate somewhat with the level of analgesia during anesthesia, but still no objective measures of analgesia exist. The drug delivery control systems used in anesthesia therefore usually ignore the analgesic component and focus on the control of the depth of hypnosis with heuristic administration of analgesic drugs through boluses or infusion.

The need for reliably monitoring of the adequacy of anesthesia and delivering the right drugs in right doses at right instants of time in order to control and balance the anesthesia is based on the quality of patient care and on economy related aspects. Balanced anesthesia reduces surgical stress and there is firm evidence that adequate analgesia decreases postoperative morbidity. Awareness during surgery with insufficient analgesia may lead to a post-traumatic stress disorder. From economical point of view, too deep an anesthesia may cause increased perioperative costs through many side-effects and extra use of drugs and time mainly in the post-operative care. Too deep a sedation may also cause complications and prolong the usage time of expensive facilities, such as the intensive care theater.

U.S. Pat. No. 6,801,803 discloses a method and device for ascertaining the cerebral state of a patient. In this disclosure, a measure derived from EMG signal data enhances and confirms the determination of the hypnotic state made using EEG signal data. As the EMG data may be computed more frequently than the EEG data, this renders ascertaining changes in the hypnotic state of the patient more rapid. State entropy (SE), which is calculated in the low frequency band up to 32 Hz, is dominated by the cortical EEG activity, while response entropy (RE), which also includes the high frequencies up to 47 Hz, represents both the cortical and muscle activity. The difference RE-SE is, therefore, a measure of the (f)EMG power, which will increase at nociception and which, therefore, may be a good measure of the suppression of the pain pathways. However, the above-mentioned dependency on the medication of the patient may render the method unusable in certain situations. As the (facial) electromyography signal is affected by neuro-muscular blocking agents (NMBAs), which suppress signaling at the nerve-muscle junctions, the EMG component of the measurement may vanish and render the method unusable, if the medication of the patient includes neuro-muscular blocking agents. Furthermore, the difference RE-SE is not specific to the suppression of the pain pathways but also reflects the overall motoric activity following any arousals—that is emotional or normal sensory evoked arousals, too. For instance, when the patient is awake and not perceiving any pain or discomfort, the RE-SE difference is typically about 8 to 10 percent. At deep hypnosis it is obvious that only painful stimuli can cause RE to differ from SE, but it is difficult to tell at which level the transition to the only-nociception induced varying difference in the deep anesthesia takes place. Furthermore, the RE-SE difference often behaves in an on-off manner without dynamic grading in between the on and off states. Therefore, the said difference suits better for event counter type applications, whereas it is less usable as a control variable for drug delivery.

U.S. Pat. No. 6,631,291 discloses a drug administration method and apparatus, in which the determination of the hypnotic level is based on a measure of the complexity of EEG signal data measured from a patient. The said measure, such as Spectral State Entropy (SE), is then used as the control variable for the delivery of a hypnotic drug. The said patent also suggests that in conjunction with the complexity of the EEG signal a measure of the electromyographic (EMG) activity of the patient may be used to improve the response time of the determination of the level of hypnosis and to speed up the control of the drug. However, U.S. Pat. No. 6,631,291 does not suggest the administration of an analgesic drug, which may have a considerable synergic effect on the level of hypnosis in the patient and, more importantly, might be the drug which, instead of a hypnotic drug, may lead to a better and balanced anesthesia in the patient. The adequacy of anesthesia in the central nervous system of a patient is thus a two-dimensional state, which should be controlled both by hypnotic and analgesic drugs in order to achieve an optimum balance for different patients, all reacting individually to these drugs.

U.S. Pat. Nos. 4,828,551 and 5,957,885 describe patient controlled analgesia (PCA) units, by which analgesic drugs are administered to the patient. The patient him- or herself controls the units to his or her optimum analgesics delivery. Therefore, the patient operating the device must be conscious to perceive and experience the pain from the tissue damage, and to relieve the pain by pressing a button or other type of delivery control actuator to release a bolus of the drug.

The prior art technology thus aim to describe the adequacy of anesthesia using a unidimensional concept for the anesthesia. Prior art solutions do not account for separate hypnotic and analgesic components, which are orthogonal, i.e. as much independent of each other as possible, and specific to the hypnotic and analgesic medications given during anesthesia. Thus the prior art methods cannot not answer the question, whether one should add or reduce the analgesics or hypnotics in order to restore a balanced anesthesia. Nowadays, personalized anesthesia requires that the anesthesiologist knows not only which drug but also how much and when to administer the drug, and that the corresponding control variables, which measure the effect of the drug choices on patient state, are available to support or directly control the drug administration.

The present invention seeks to alleviate or eliminate the above drawbacks and to bring about a novel mechanism for monitoring, evaluating and controlling anesthesia with balanced delivery of hypnotics, analgesics, and muscle relaxants.

SUMMARY OF THE INVENTION

The present invention seeks to provide a novel mechanism for determining and controlling the anesthetic state of a patient. The present invention further seeks to provide a control mechanism which is able to take into account the synergic effects of the analgesics and hypnotics to maintain high quality, balanced anesthesia.

In the basic embodiments of the present invention, the determination of the anesthetic state of a patient is based on two diagnostic indices determined for the patient: an index of nociception indicative of the level of analgesia in the patient and an index of hypnosis indicative of the level of hypnosis in the patient. The combination of the prevailing values of the said two indices determines the current anesthetic state of the patient. As discussed below the state defined by the combination of the index values may be utilized in various ways depending, for example, on whether the state is determined in a closed or in an open loop system/apparatus. For example, the state may be determined as a location in a two dimensional plot, such as a coordinate system, in which one of the axes represents the index of nociception and the other axis the index of hypnosis. Thus, the location is indicative of the anesthetic state of the patient and may be compared with one or more targeted locations in the plot, which represent a state of balanced anesthesia. For control purposes the measured location may thus be compared with a predetermined permissible domain or point within the said two-dimensional plot. The comparison may include the determination of at least one displacement measure, which may indicate, for example, the distance and direction of the measured location from at least one targeted location. In a further embodiment of the invention, the space in which the location is defined comprises three dimensions, the third dimension representing the neuromuscular blockade of the patient. Although the anesthetic state of the patient may be indicated simply by indicating to the anesthesiologist the values of all indices employed, the location that the said values define is useful in a closed loop control system and informative in an open loop control system.

Thus one aspect of the invention is providing a method for determining the anesthetic state of a patient. The method includes the steps of establishing values for a set of diagnostic indices, the set including at least two diagnostic indices of which a first diagnostic index is indicative of the hypnotic level in a patient and a second diagnostic index of the level of analgesia in the patient, whereby at least two index values are obtained and employing the at least two index values for indicating the anesthetic state of the patient.

Another aspect of the invention is that of providing an apparatus for determining the anesthetic state of a patient. The apparatus includes first means for establishing values for a set of diagnostic indices, the set including at least two diagnostic indices of which a first diagnostic index is indicative of the hypnotic level in a patient and a second diagnostic index of the level of nociception in the patient, whereby at least two index values are obtained and second means for employing the at least two index values for indicating the anesthetic state of the patient.

By means of the invention, the anesthetic state of a patient may be determined in a way that enables balanced control of the administration of hypnotic and analgesic drugs to different patients and thus an optimum balance between the hypnotic and nociceptive levels in different patients. In addition to the anesthetic levels of sedation, the mechanism of the invention may also be employed in connection with lighter levels of sedation, where sedation refers to a drug-induced state of a patient, which includes two components, analgesia and hypnosis.

A further aspect of the invention is that of providing a computer program product by means of which known measurement devices may be upgraded to enable the determination of the anesthetic state of a patient. The program product includes a first program code portion configured to establish values for a set of diagnostic indices, the set including at least two diagnostic indices of which a first diagnostic index is indicative of the hypnotic level in a patient and a second diagnostic index of the level of nociception in the patient, whereby at least two index values are obtained and a second program code portion configured to employ the at least index values for indicating the anesthetic state of the patient.

Still further aspects of the invention are those of providing a method and a system for controlling the anesthetic state of a patient. The method includes the steps of establishing values for a set of diagnostic indices, the set including at least two diagnostic indices of which a first diagnostic index is indicative of the hypnotic level in a patient and a second diagnostic index of the level of analgesia in the patient, whereby at least two index values are obtained and controlling, based on the at least two index values, administration of at least one drug to the patient, wherein the at least one drug belongs to a group of drugs including at least one analgesic drug and at least one hypnotic drug. The system in turn includes means for establishing values for a set of diagnostic indices, the set including at least two diagnostic indices of which a first diagnostic index is indicative of the hypnotic level in a patient and a second diagnostic index of the level of analgesia in the patient, drug delivery means for administering at least one drug to the patient, wherein the at least one drug belongs to a group of drugs including at least one analgesic drug and at least one hypnotic drug, and control means for controlling the drug delivery means based on the at least two diagnostic indices.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIGS. 1 to 15 in the appended drawings, wherein:

FIG. 5 illustrates the implementation of one embodiment of the normalization transform employed in the determination of the index of nociception;

FIGS. 6a to 6d illustrate one embodiment of the normalization process employed in the determination of the index of nociception;

FIG. 7 illustrates a further embodiment for determining the index of nociception;

DETAILED DESCRIPTION OF THE INVENTION

Figure 1:
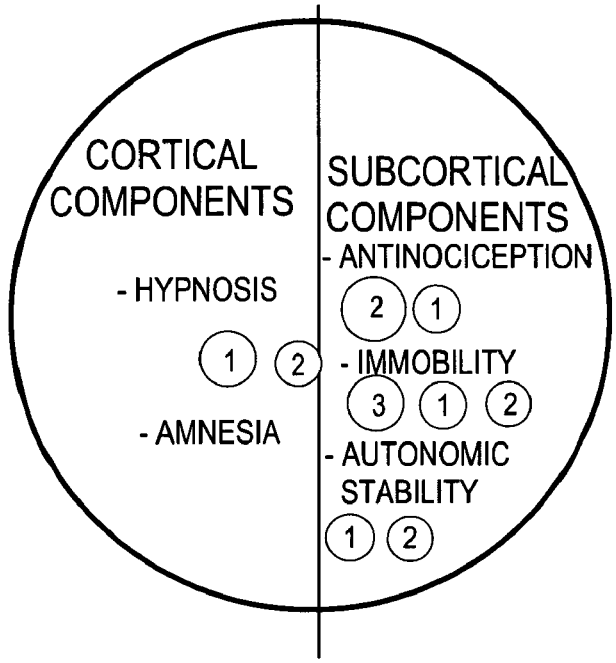
FIG. 1 illustrates the concept of anesthesia.

FIG. 1 illustrates the concept of the quality of anesthesia. According to the current comprehension, the anesthesia includes five different components: hypnosis (i.e. unconsciousness), amnesia, antinociception, immobility, and the stability of the ANS. The first two components, the hypnosis and amnesia, are of cortical origin and are indicative of cortical activities and processes. The suppression of the cortical activity is obtained by drugs, which typically affect neural signaling globally in the brain. The drugs may activate the natural inhibitory GABA receptor system in the brains or prevent, by an unknown mechanism, neural signaling in the synapses between the neurons. For this reason, the drugs often also affect other parts than the cortex in the brain, thereby also suppressing subcortical activity and processes.

The other components in the anesthesia model, which are indicative of sub-cortex related activity in the patient, are much more specific and often relate to altering, modulating or blocking neural signaling at certain receptor or neurotransmitter level. These components can be affected selectively by different specific drugs. For instance, antinociception, i.e. the suppression of the neural transmission in the pain pathways, is achieved by opioid drugs, which affect the opioid/enkephalin receptors and activate the descending pathways, which block or modulate the nociceptive stimuli in the spinal cord. Furthermore, the NMBA drugs block the neural transmission in peripheral neuro-muscular junctions, which results in one kind of specific immobility, paralysis of a patient. The stability of the ANS and the antinociception are closely related, since noxious stimulation in deep anesthesia may cause hemodynamic and hormonal instability. The stability of the ANS is therefore also advanced by opioid drugs and by several other drugs, which may affect specifically the parasympathetical or sympathetical activities of the ANS.

FIG. 1 also shows the drugs associated with each component of the anesthesia model by showing numbered circles, in which number one refers to hypnotics, number two to opioids, and number three to NMBAs. Although many drugs may be involved in achieving an adequate level of the cortical and subcortical activity, the adequacy of anesthesia is often managed only by a gas anesthetic agent or other hypnotic agent, which dominantly affects the cortical activity, and by an opioid, which selectively modulates the pain pathways at subcortical level, and by a NMBA drug, which induces immobility by blocking neuronal transmission in peripheral nerve-muscle junctions. The effects of a hypnotic agent may be monitored, for instance, by the above-described measurements based on calculation of EEG entropy and the neuromuscular blockade by an NMT (NeuroMuscular Transmission) measurement. The hypnotic and NMBA drugs may then be administered based on these measurements.

The present invention provides a mechanism for ascertaining the anesthetic state of a patient for the control of the above-mentioned drugs related to high quality anesthesia. Depending on the embodiment of the invention, the anesthetic state determined may be utilized in a closed or open loop drug administration system. The closed loop system here refers to a system in which the administration of the drugs is automatically controlled by a control unit in response to the anesthetic state determined. An open loop system in turn refers to a system in which an anesthesiologist observes the anesthetic state and administers the drugs to the patient. Thus in open loop systems the mechanism of the invention serves as a decision-support tool for the anesthesiologist.

Figure 2:
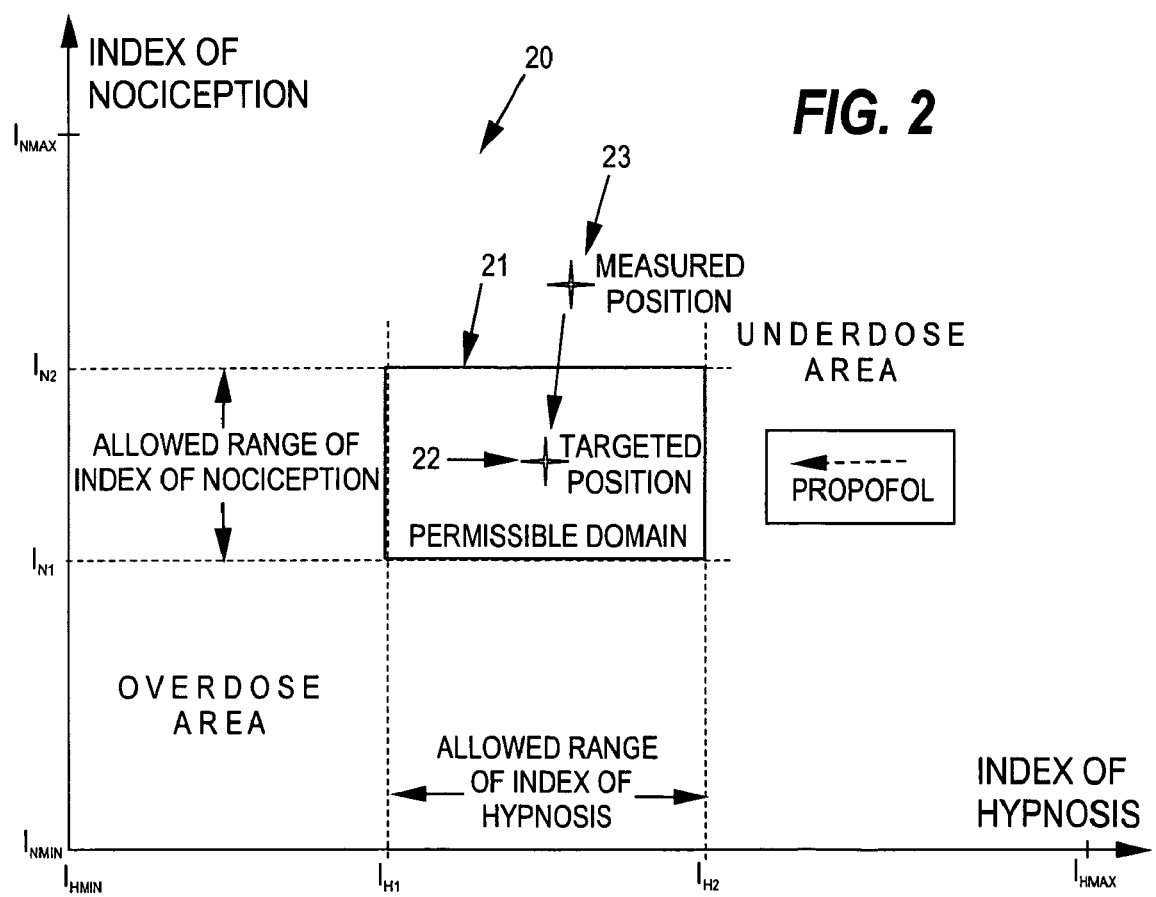
FIG. 2 illustrates the control principle according to the invention.

FIG. 2 illustrates one embodiment of the control mechanism in the basic embodiments of the invention. In the said basic embodiments, two diagnostic indices are determined for a patient: an index of nociception indicative of the level of analgesia in the patient and an index of hypnosis indicative of the level of hypnosis in the patient. The anesthetic state of the patient is then determined by determining the location defined by the prevailing values of the two indices in a two-dimensional space 20, i.e. a plane, a coordinate system or a defined box in the value space, in which one of the axes represents the level of analgesia and the other the level of hypnosis. Both indices have predetermined minimum and maximum values. In the example of the FIG. 2, the index for analgesia may be between a minimum value of $I_{NMIN}$ and a maximum value of $I_{NMAX}$, while the index for hypnosis may be between a minimum value of $I_{HMIN}$ and a maximum value of $I_{HMAX}$.

The determination of the indices is discussed below after the discussion related to the embodiment of FIG. 3. As described there, the index describing the level of hypnosis may be the above-described Bispectral Index by Aspect Medical or the Entropy Index by Datex-Ohmeda, while the index of analgesia is a novel index of nociception (IoN).

Depending on the type of the surgery in question, the anesthesiologist may define a permissible value range for both indices. It is assumed in the example of FIG. 2 that the permissible values of the index of nociception are between $I_{N1}$ and $I_{N2}$ and the permissible values of the index of hypnosis between $I_{H1}$ and $I_{H2}$. Consequently, the said permissible values define a permissible domain 21 within the two-dimensional space. This domain represents the state of a patient with adequate and balanced hypnosis and analgesia. The said area is typically in the middle of the coordinate system, whereas the areas near the origin represent overdose situations (Entropy Index or Bispectral Index is near $I_{HMIN}$ (=0) and IoN is near $I_{NMIN}$) and the areas with high index values represent underdose situations (Entropy Index or Bispectral Index and IoN are near their corresponding maximum values $I_{HMAX}$ (=100) and $I_{NMAX}$). Generally, the form and size of the permissible area, i.e. the area of balanced anesthesia, may vary. It may be, for example, curve-shaped or a circle. The anesthesiologist may also define a targeted point 22, which is the point within the permissible area to which the state of the patient should be controlled.

The anesthetic state of the patient is determined by measuring the current values of the two indices. The current values of the indices define a point (location) 23 in the two-dimensional space/plot. If the anesthesiologist wants to move the state from the current location 23 to the targeted location 22, he or she needs to consider which drug to give to the patient. In this particular example, the right choice could be a bolus or increased infusion of an analgesic drug that would decrease the index of nociception but leave the index of hypnosis intact or decrease it slightly. The level of hypnosis would most likely be slightly affected as the analgesics and hypnotics have synergic effects. The degree of synergy is typically dependent on the level of hypnosis.

The state of the patient in the above-described two-dimensional space may thus be utilized to administer at least one drug to the patient. Pharmacokinetic (PK) and especially pharmacodynamic (PD) modeling may be used in connection with the selection of the drug(s) to be administered. Propofol, for example, is a rather pure hypnotic drug and will therefore shift the patient state to the left due to the primary effect and down due to the synergic effect. Thus, different drugs may be represented by corresponding vectors, which will change the state of the patient, i.e. the location in the plot, in a certain way. As the effect of the drugs may be evaluated, the choice of the drugs to be administered, as well as the corresponding dosages, may be made based on the distance and direction between the measured point 23 and the targeted point 22. For example, the system may evaluate a first measure indicative of the difference in the level of nociception between the measured point and the targeted point and a second measure indicative of the difference in the level of hypnosis between the measured point and the targeted point, and select the drug(s) and/or dosage(s) to be administered based on the two measures and the PK/PD models. As discussed below, the system of the invention may also assist the anesthesiologist to make the right selections. It is also to be noted here that in total intra-venous anesthesia it is only possible to increase the drug effects, whereas the decrease takes place at the speed of the metabolism or excretion of the drugs. In gas anesthesia, it is also possible to decrease the drug effects by increasing ventilation.

Figure 3:
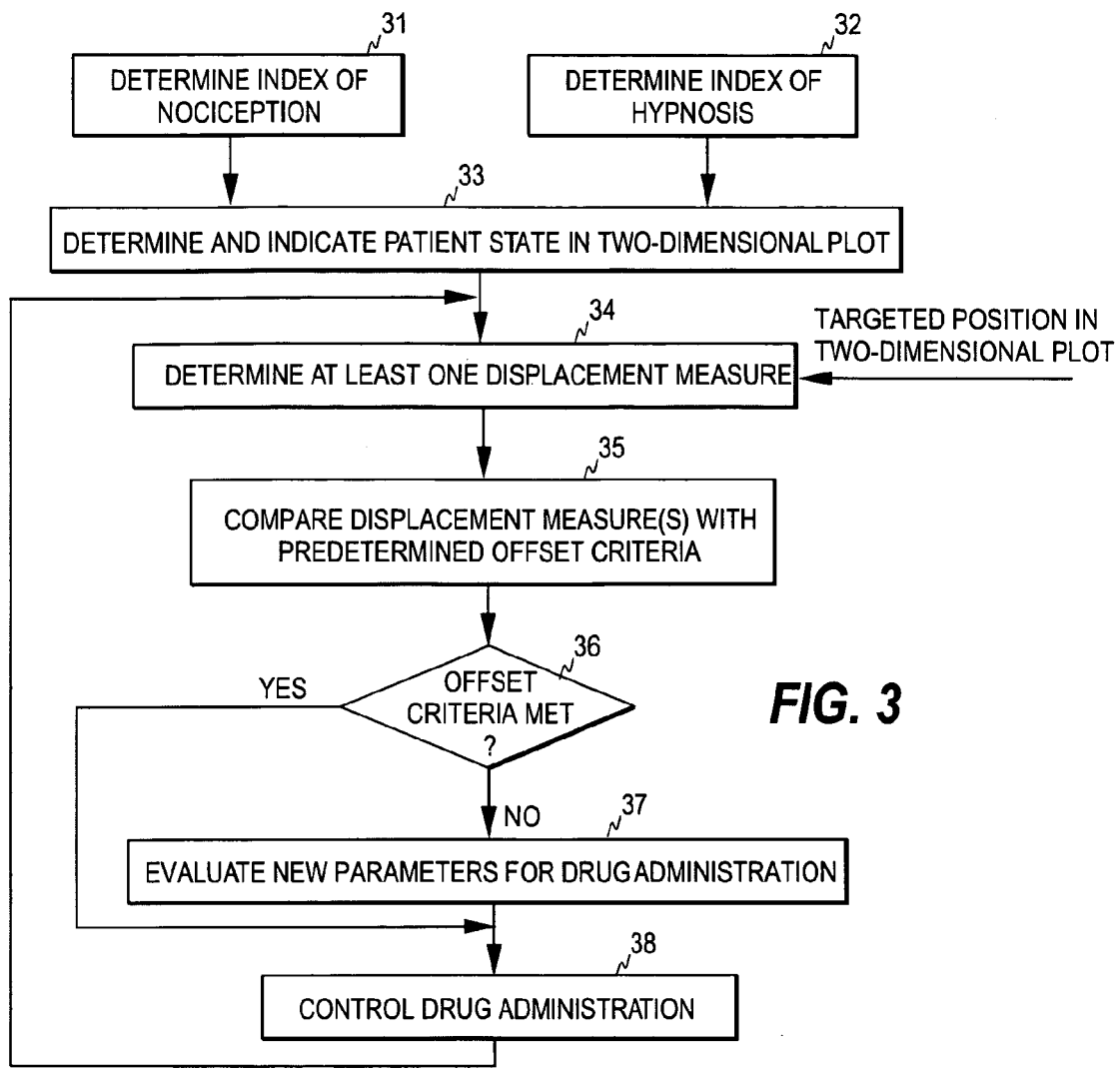
FIG. 3 is a flow diagram illustrating one embodiment of a control method according to the invention.

FIG. 3 illustrates one embodiment of the control method according to the invention. The two indices, the index of nociception and the index of hypnosis are first determined (steps 31 and 32). The index of hypnosis may be defined in a known way but the index of nociception is preferably a novel analgesia monitoring parameter, which directly measures the patient stress responses to nociception. This is discussed after FIG. 3. When the two indices have been determined, the anesthetic state of the patient is determined by determining and indicating the prevailing location 23 in the two-dimensional plot defined by the indices (step 33). The control process then defines at least one displacement measure indicative of the displacement of the prevailing location from at least one predetermined reference point in the plot (step 34). Typically, the said at least one measure includes at least two measures indicative, respectively, of the distance and direction of a predetermined targeted location or domain from the prevailing location. The displacement measure(s) obtained is/are then compared with predetermined offset criteria/criterion, which the anesthesiologist has defined in advance (step 35). For example, the offset criteria may state that if the state of the patient is within the permissible domain or if the state of the patient has not been continuously outside the permissible domain longer than a predetermined maximum time limit, the criteria are met. Thus, it is possible to allow short-term displacements from the permissible domain. Therefore, the at least one displacement measure may be defined for several index pairs at step 34. If the predetermined criteria are met, the process continues to monitor the state of the patient in the two-dimensional plot. However, if the criteria are not met, the control process evaluates, based on the displacement measures, the displacement history and the history of the drug delivery, new parameters for the drug administration (step 37). These parameters define a change in the drug administration process, the change being designed to transfer the state of the patient from the current location to the targeted location. The administration process is then controlled according to the new parameters (step 38). For safe drug delivery, the history of the drug infusions, the total amounts of drugs, and the state of anesthesia should be considered in conjunction with the evaluation of the new set values for the drug administration. For instance, if the patient state is out of the targeted area, which is normally indicative of a need for a change of a drug, the drug administration parameters may be kept unchanged, if a change in the drug administration towards the right direction has been made recently, or if the anesthetic state is already on the move towards the targeted area.

Figure 4:
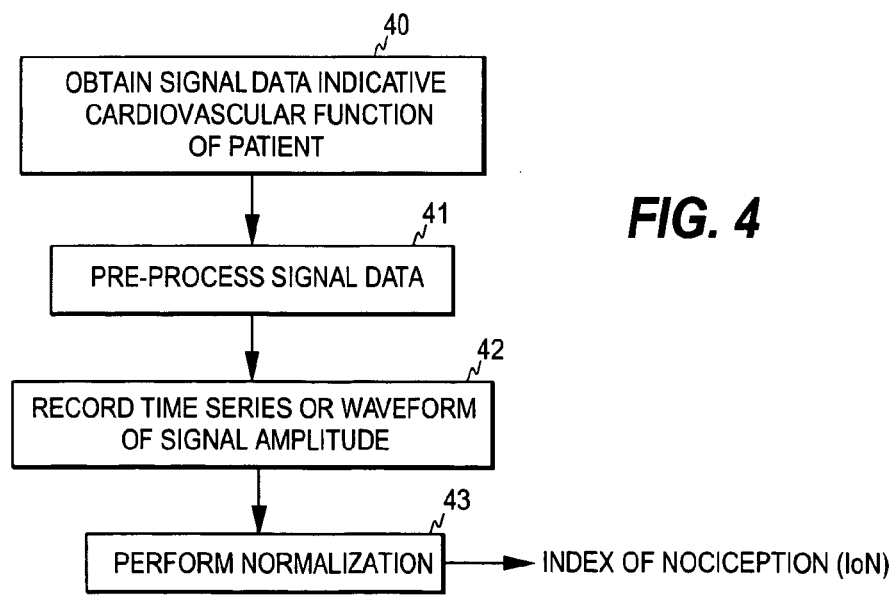
FIG. 4 illustrates one embodiment for determining the index of nociception.

The index of nociception may be determined as is disclosed in Applicant's co-pending U.S. patent application Ser. No. 11/089,528, filed Mar. 24, 2005 FIG. 4 illustrates one embodiment of the present invention, in which the index of nociception, which is directly indicative of the amount of nociception, is formed by means of one normalized signal. In this embodiment, signal data indicative of the function of the cardiovascular system of the patient is first obtained from the patient (step 40), since changes in the level of nociception are reflected in such signals. Such signals include a plethysmographic signal, such as a photoplethysmographic (PPG) signal, a blood pressure (BP) signal, an ECG signal, or a Laser Doppler flow signal in peripheral tissues.

The cardiovascular system includes the heart, veins, arteries, and blood. Its main function is to transport oxygen and nutrients to all areas of the body and carry away carbon dioxide to the lungs and other wastes to the kidneys for excretion. The functions of the cardiovascular system induce a plurality of physiological signals that may be recorded to obtain information of the cardiovascular status of the subject. Such physiological signals include signals indicative of the peripheral blood circulation of the subject, such as a plethysmographic signal or a blood pressure signal. Blood pressure pulsation caused by the beating heart or air pressure variations in the lungs, for example, are mediated to the peripheries of the body through the vascular system. The tone of the vascular system regulates the conduction of the pulsation. Changes in the vascular tone form an independent source of pulsation detected in the peripheries of the body. Typical peripheral locations for the recording of the pulsation are finger tips and ear lobes. Therefore, most of the signals indicative of the function of the cardiovascular system, such as a PPG signal, a BP signal, or a Laser Doppler flow signal are also indicative of the pulsative component of the peripheral blood circulation.

The measurement of the signal waveform data may be implemented in a conventional manner, i.e. while the patient connected to a patient monitoring system, the signal waveform data is recorded and stored in a memory of a monitoring device. In order for the method to be quick enough, the measurement is such that new signal values are received frequently, for example at about 100 samples/sec.

The recorded waveform data may then be pre-processed at step 41 for filtering out some of the frequency components of the signal or for rejecting artifacts, for example. This step is not necessary, but may be performed to improve the quality of the signal data.

Next, the pulse amplitude of the waveform signal is extracted for each pulse beat at step 42, whereby a time series of the amplitude of the pulsative component of the peripheral blood circulation is obtained.

The said time series is then subjected to a normalization process in step 43. The normalization process here refers to a process that scales the input signal values to a predetermined output value range, such as 0 to 100.

The normalization process is further patient-adaptive, i.e. it adapts to the patient in question. In order to obtain the adaptation to the patient, the normalization transform is made dependent on time series data recorded previously for the same patient. For example, the normalization transform may be dependent on the mean and variance of the amplitude of the pulsative component, which are defined based on data measured earlier during a measuring period of a predetermined length, such as 5 minutes, or from a certain event to the present, such as since the beginning of the surgery.

A third characteristic feature of a typical normalization transform is that it emphasizes slow changes in the input signal. This is accomplished by making output values that correspond to the mean or center of the input value range relatively more sensitive to input value changes than the values in the tail regions. This mechanism enhances small changes or trends in the input values and damps large, jump-like responses in the input signal. The transform is thus especially suitable for detecting relative slow changes, i.e. trends, in the patient status, such as drug affected changes in the level of antinociception.

To sum up, a typical transform applied to the input signal at step 43 has three different properties:
- the transform is a normalization transform, i.e. it forces the input values to a predetermined output value range;
- the transform is patient-adaptive, i.e. as the transform is made dependent on signal data measured earlier from the current patient, it adapts to the patient; and
- the transform emphasizes slow changes in the input signal, which facilitates the monitoring of the trend in the clinical state.

A transform fulfilling the above criteria may be accomplished by various techniques, which include the use of a parameterized function transform or the use of a so-called histogram transform. In the following the histogram techniques are described with reference to FIGS. 6 to 7d.

The above-described three basic properties of the transform are best achieved by using a histogram transform in step 43. In a histogram transform, an input array 51 and an output array 52 are formed, as is shown in FIG. 5. The input array (buffer) comprises i input elements, also termed bins, storing, respectively, i input values sorted in ascending or descending order, while the output array (buffer) comprises fixed index values sorted in ascending or descending order and stored in i output elements. In the example of FIG. 5, the index values of the output buffer range from 0 to 100 corresponding to the total number of values in the input buffer, i.e. i=101. The values of the time series of the amplitude of the pulsative component, i.e. the values obtained from step 42, are thus forced to the value range of the output buffer. This may be implemented in three different ways depending on whether full adaptation, partial adaptation, or no adaptation to the incoming signal is utilized. These embodiments of the histogram transform are discussed briefly in the following.

In full adaptation, the latest signal values of the time series of the amplitude of the pulsative component are stored in the input array so that the value of each new data point obtained in the time series replaces the oldest value in the input array. When a new value is obtained from step 42, the oldest value in the input array is deleted, and the remaining values and the new value are sorted to form a new input array. The output value of the transform is then obtained by means of the output array as the index value that corresponds to the location of the new value in the input array. In this way, the level of the signal may change but the output values remain between the lowest and highest indices, i.e. in this example between 0 and 100. The time series obtained from the output array 52 may thus be such that the mean value is constant and the variability of the amplitude is limited to a certain range and certain distribution around the mean value. For instance, a Gaussian or even distribution with a desired mean value may be used for the values output from the transform.

Full adaptation may also be implemented by a parameterized function transform, the mean and standard deviation (SD) as parameters of the transform function. The parameterized function transform is discussed in more detail in the above-mentioned co-pending patent application having the same filing date as the present application. If a histogram transform is used, no patient-specific parameters are needed, since the sorting of previous signal data makes the histogram transform patient-adaptive. If a parameterized transform is used, no sorting of input data is needed.

In case no adaptation to the incoming signal is used in the histogram transform, the input array remains the same regardless of the incoming signal values. The input array may be formed based on values measured from a large patient group, which yields a wider distribution of input values than what is typically obtained for one patient. Thus, instead of storing the latest i values of the same patient, the input array may store i fixed values representing the distribution of the values of the amplitude of the pulsative component among a (large) group of patients. When a new value is obtained in the incoming time series from step 42, the corresponding output value of the transformation is obtained in the above-described manner as the index value that corresponds to the location of the new value in the sorted input array. Although this embodiment of the histogram transform is not patient-adaptive, different input arrays may still be defined for different patient groups, such as children or adults, and different input arrays may further be defined for each patient group according to various other parameters, such as the type of the sensor used or the peripheral site of the sensor (ear, finger, toe). Similar non-adaptive transforms may be implemented by means of the parameterized transform. In this case the transform includes one or more parameters, whose value(s) depend on the patient group in question, and possible also on other parameters, such as the sensor type or site.

Partial adaptation to the incoming signal refers to the combination of the above two methods. An embodiment of the partial adaptation is illustrated in FIGS. 6a to 6d. FIG. 6a illustrates a parameter distribution curve 61 for a large number of patients representing a certain patient group in general anesthesia. The size of the patient group may be very large representing about 1000 patients, for example. The range of the parameter values, in the figures from 0 to 300, is advantageously selected to be much wider than the actual range obtained during a surgery of an individual patient. During the surgery the same parameter, i.e. in this case the amplitude of the pulsative component of the blood circulation, is measured and a histogram distribution is created using the same parameter value bins as in the large population average. This distribution for the individual patient may contain a fixed number of values, e.g. 300, and the distribution may be updated using the full adaptation method described above. It is also possible that a cumulative distribution of the parameter values of the individual patient is collected and that the distribution counts so obtained are scaled down to a predetermined match in total counts to the patient group distribution. In such a case, the individual patient distribution may represent the parameter values since the beginning of the surgery till the current moment during surgery. An example of a normalized patient-specific distribution curve 62 obtained during a surgery is presented in FIG. 6b.

The normalized patient-specific distribution is then added in a predetermined proportion to the normalized patient group distribution, and an average total distribution curve 63 is formed, as shown in FIG. 6c. In this example, the two normalized distributions are weighted equally in the total distribution. For calculating the input parameter value array for the partially adapted histogram transform a cumulative sum of the average total distribution is then constructed as shown in FIG. 6d. If the histogram transform arrays are 101 element long, for example, the new values for the input bins of the histogram transform can be obtained by projecting the cumulative sum values 0, 1, 2, . . . , 100 of the Y-axis to the parameter value axis (X-axis), as is shown by dashed lines in FIG. 6d. The X-axis values obtained in this way form the input values of the input array for the histogram transform. The actual histogram transform is then executed without adaptation. In this embodiment, input values for the input array are thus obtained by adding a group distribution curve to the patient-specific distribution curve and then defining the input values for the input array by means of the cumulative distribution function of the summed distribution curve. Once being defined in the above-described manner, the input values of the input array remain fixed for a predetermined update interval, which can typically represent about 100 new individual parameter values.

The proportions of the adaptive and non-adaptive values in the combined input may vary. The same applies to the size of the steps between consecutive (fixed) values stored in the input or output arrays. For example, in the example presented in connection with FIGS. 6a to 6d each consecutive input array bin contained one percent of the input values. However, the steps may also be such that a certain other percentage of values is within each step (i.e. in each bin), in which case the step may be smaller around one range of the input values and correspondingly larger around another range of the input values. The median value of the output signal, i.e. the center index of the output array, may be transformed to a desired output value, such as 50. The distribution of the output values may be specified according to the needs of the application.

As the adaptation to the patient is a preferred property for the normalization transform in the embodiments of FIG. 4, fully or partially adaptive normalization transforms are the preferred embodiments in step 43 of FIG. 4. As discussed above, in case of a partially adaptive transform, the normalization transform to be used at each time may depend on the patient, i.e. to which patient group the patient belongs, on the sensor used, and/or on the location of the sensor (finger or ear).

A generalized form of a partial patient adaptive histogram transformation may thus be presented as follows: H(patient adaptive transformation)=A*H1(large patient population)+B*H2(history data since the beginning of the surgery)+C*H3 (history data over the last M minutes), in which the first reference histogram H1 is for a large population group of similar patients (adults, children, infants, etc.) or for a particular type of sensor or equipment (PPG finger sensor, PPG ear sensor, etc.), the second reference histogram H2 is for the parameter values recorded since the beginning of surgery or anesthesia (long history data), and the third reference histogram H3 is for the parameter values recorded over the last M minutes, such as 5 minutes (short history data). The multiplying factors (A, B, and C, where A+B+C=1) are the relative weights of the separately normalized histogram distributions. The principal reason for the usage of a patient population histogram is that it contains the widest distribution of the parameter values, and thereby represents the allowable parameter range of the input values. The history data since the beginning of the anesthesia or surgery substantially sets each patient to the same norm. The histogram pertaining to the last M minutes allows a fast adaptation to trend-like parameter changes within one patient and thereby sets each phase of the surgery to a same equivalent norm, regardless of the absolute average value of the parameter in the time window of M minutes.

In the above embodiments of FIG. 4, the output signal of the normalization transform thus directly indicates the level of the antinociceptive component of anesthesia in the patient. In this context, the said output signal is termed the first normalized signal.

In further embodiments of the present invention, the specificity of the index of nociception to noxious stimulation and to analgesic drug concentration may be improved by producing a composite indication based on the first normalized signal and at least one other normalized signal made commensurable with the first normalized signal. This is discussed in the following.

In the second group of embodiments for determining the index of nociception, the composite indication is formed based on two normalized signals. In these embodiments, which are illustrated in FIG. 7, the time domain is taken into account by producing the composite indication based on the first normalized signal and a normalized pulse interval, which is in this context termed the second normalized signal. The pulse interval here refers to the beat-to-beat interval of the physiological signal in question. As the physiological signal employed to obtain the first normalized signal may be a plethysmographic signal, an ECG signal, or a blood pressure signal, the same physiological signal data may be used to derive the time series of the pulse interval. Thus, in this case the signal may be supplied from step 41 directly to step 72, in which the time series of the pulse interval is generated. If the first and second normalized signals are based on different physiological signals, a pre-processing step 71 similar to step 41 may precede step 72.

The time series of the pulse interval is then subjected to a normalization transform at step 73 to obtain a time series of a normalized pulse interval.

The transform applied to the pulse interval at step 73 is typically similar to the transform applied to the amplitude time series in step 43. The transform is thus typically a fully or partially adaptive normalization transform, which may be implemented as a parameterized transform or as a histogram transform.

The normalized pulsative component and the normalized pulse interval are then combined at step 74 to form a composite indicator that serves as the index of nociception. This may be performed by calculating a weighted average of the two normalized values for each data point pair obtained from the two time series.

To give an example of preferred values of the two weights, the weighted average WA may be calculated for example as follows:

$$WA = -(0.43*RRI(\text{norm}) + 0.57*PPGA(\text{norm})) + 100,$$

where norm refers to normalized parameter values.

The specificity of the index of nociception to noxious stimulation and to analgesic drug concentration may further be improved by adding a third normalized parameter to the group of normalized parameters whose weighted average forms the index of nociception. It is also possible to use more than three normalized signals for the determination of the index of nociception, by adding more physiological signals from among the signals mentioned above. For a more detailed description of the embodiments employing three or more normalized parameters for determining the index of nociception, reference is made to the above-mentioned co-pending patent application having the same filing date as the present patent application.

The index of hypnosis may be determined similarly as in the above-mentioned U.S. Pat. Nos. 6,631,291 or 6,801,803. In other words, at step 32 a parameter is defined, which characterizes the amount of disorder or complexity in EEG signal data obtained from the patient. Currently, the use of spectral entropy is deemed advantageous for this purpose due to the computational simplicity as compared to the other techniques available. However, other quantifications, such as fractal spectrum analysis, Lempel-Ziv complexity or bispectral or multispectral analyses may also be used for this purpose. As a more detailed discussion of the various mathematical techniques available for obtaining such a parameter can be found in the above-referred patents, these methods are not discussed in detail in this context.

The index of nociception output from step 31 (i.e. from step 43 of FIG. 4, step 74 of FIG. 7) functions intuitively as showing increased values when noxious stimulation increases or when the analgesics drug concentration in blood decreases at unchanged stimulation level and, vice versa, showing decreased values when noxious stimulation decreases or when the analgesics concentration in blood increases at constant stimulation level. In the above-described manner the two indices can be made to vary between two fixed limit values, such as zero and one hundred, wherein zero is indicative of too strong a medication and one hundred of too mild a medication, or vice versa. It is to be noted here that the determination of the index of hypnosis does not necessarily require a separate normalization, since the calculation of the complexity measure, such as entropy, has an intrinsic feature of keeping the output value within a certain output range, such as from 0 to 100.

Figure 8:
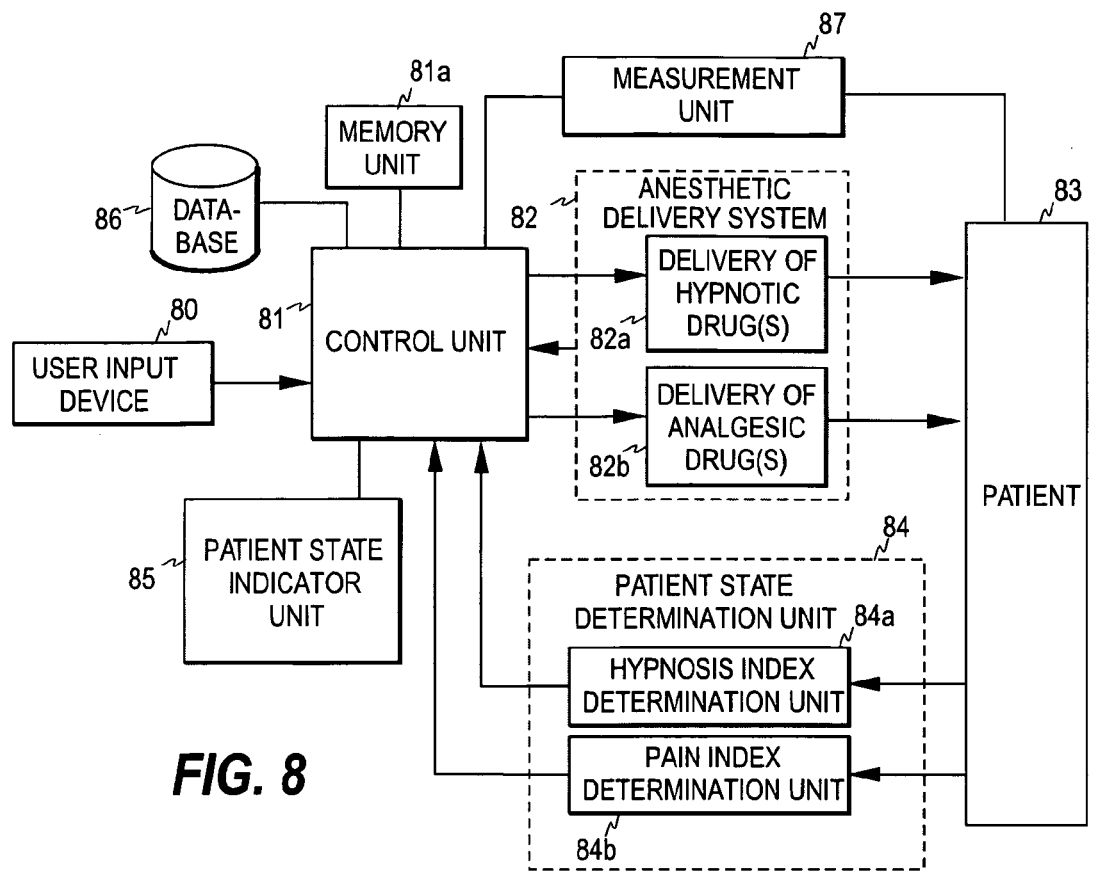
FIG. 8 is a schematic diagram showing one embodiment of a closed loop drug administration control according to the invention.

FIG. 8 is a schematic diagram showing one embodiment of a closed loop drug administration system of the invention. A control unit 81, which is provided with a control memory 81*a*, controls a drug delivery system 82 comprising a first delivery unit 82*a* for delivering hypnotic drugs and a second delivery unit 82*b* for delivering analgesic drugs. The anesthesiologist may operate the system through a user interface comprising a user input device 80 from which the anesthesiologist may supply input parameters to the control unit. The user interface may further comprise a display or another appropriate indicator unit 85, which is controlled by the control unit. The physiological data measured from a patient 83 is supplied to a patient state determination unit 84, which comprises, at least on a logical level, a hypnosis index determination unit 84*a* and an analgesia index determination unit 84*b*. The former determines the index of hypnosis and supplies it to the control unit, while the latter determines the index of nociception and supplies it to the control unit. The control unit determines the location corresponding to the patient state in a two-dimensional plot and displays the location on the screen of the display unit 85 in the manner discussed above in connection with FIG. 2. The control unit 81 retrieves drug administration data, such as the amounts administered, from the drug delivery system and stores the data for setting new parameters for the delivery unit. As also discussed above, the determination units or the control unit may filter out short-term deflections in the index values to obtain index values that represent some form of average calculated based on two or more index values.

The control unit also compares the determined location with the input parameters defining the targeted location(s) and controls the anesthetic delivery system to shift the state towards the targeted state or to maintain the state of the patient in the targeted domain. Although the software and data needed for the control may be stored in the control memory, the control unit may further be provided with a separate database 86 holding information about the pharmocodynamic and pharmacokinetic properties of the drugs to be administered. For the controlling and/or pharmacodynamic and/or pharmacokinetic modeling the system may further be provided with one or more measurement units 87, which provide measurement information for the control or modeling process. Such a measurement unit may be, for example, a gas agent measurement unit providing feedback information about the concentration of an inhaled anesthetic agent. The anesthetic delivery system may comprise more than two delivery units depending on the drugs to be administered. Furthermore, the delivery system may also comprise one delivery unit only. It is thus also possible that the state of the patient in the two-dimensional state is employed to control the administration of either an analgesic drug or a hypnotic drug only. In case of an intravenously administered drug a delivery unit typically comprises a motor driven infusion pump, while in case of an inhaled drug the delivery unit typically comprises a vaporizer. In practice, the control unit may be PID controller, for example.

Figure 9:
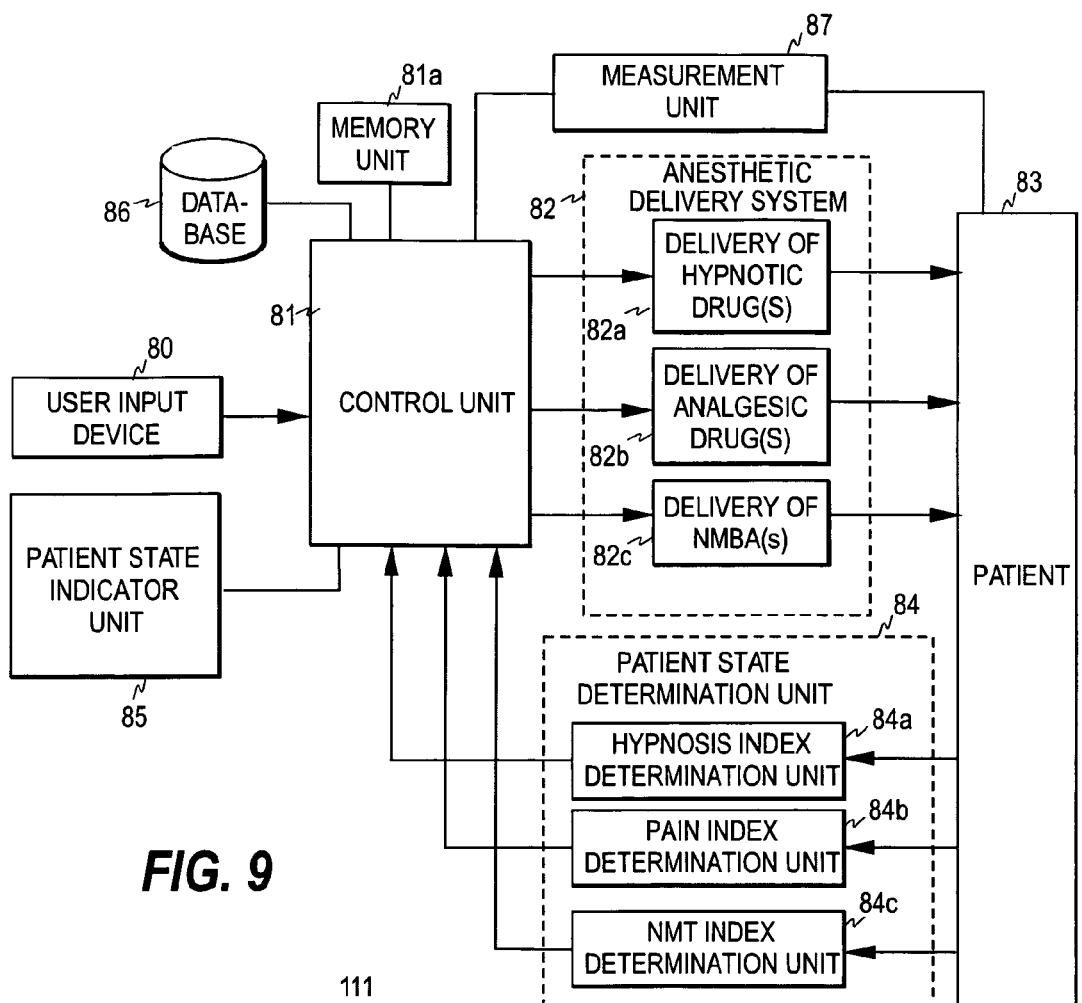
FIG. 9 is a schematic diagram showing another embodiment of a closed loop drug administration control according to the invention.

The space in which the anesthetic state of a patient is determined may also comprise more than two dimensions. FIG. 9 illustrates an embodiment in which a third dimension is introduced by adding to the patient determination unit 84 an NMT index determination unit 84*c*, which determines an NMT index indicative of the level of the neuromuscular block, and supplies the index to the control unit. The NMT index determination unit may comprise any commercially available NMT module that provides a quantitative measurement of the muscle response and thus provides an output which is between predetermined minimum and maximum limits. Thus in this case the control unit determines the state of the patient in a three-dimensional space, displays the state through an indicator unit 85, and controls the anesthetic delivery system, which now includes a further delivery unit 82c for the administration of one or more neuromuscular blocking agents.

Figure 10:
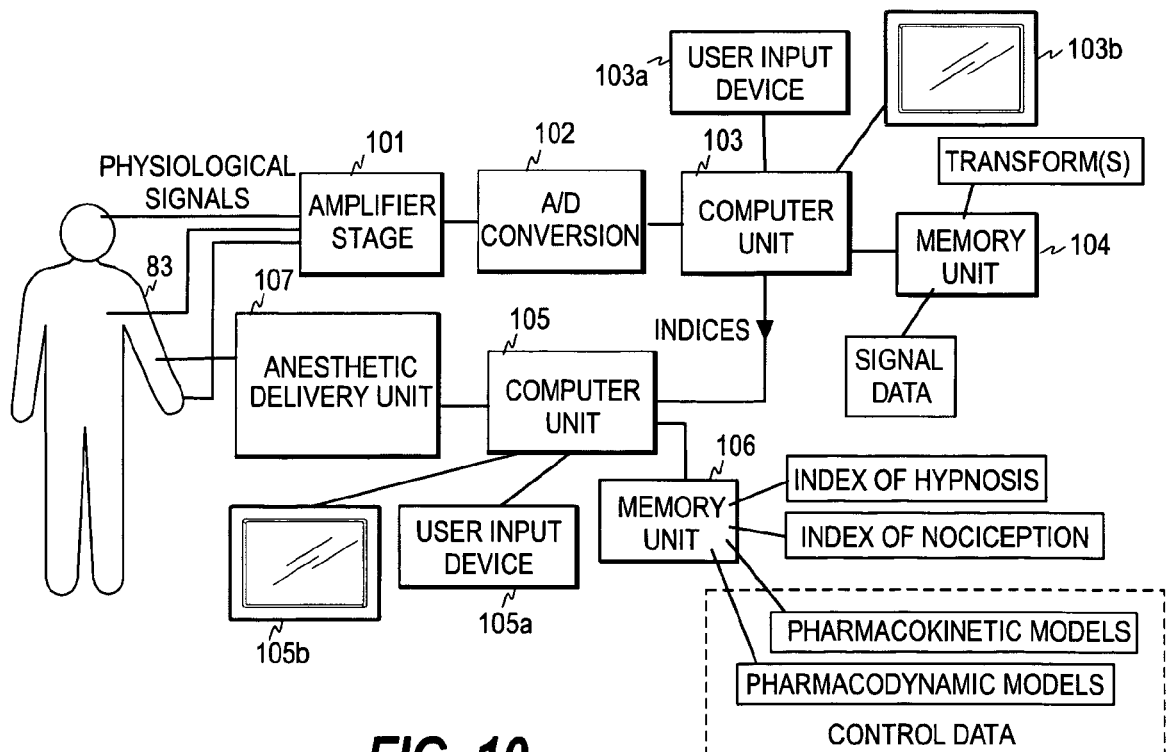
FIG. 10 illustrates an example of a closed loop drug administration system according to the invention.

FIG. 10 illustrates a further embodiment of a closed loop drug administration system of the invention. The physiological signals obtained from one or more sensors attached to a patient 83 are supplied to an amplifier stage 101, which amplifies the signals before they are sampled and converted into digitized format in an A/D converter 102. As discussed above, the physiological signals measured from the patient include typically an EEG signal for determining the index of hypnosis and at least one signal selected from a group including a plethysmographic signal, a blood pressure signal, a respiration signal and an ECG signal for determining the index of nociception. The digitized signals are supplied to a computer unit 103 which may comprise one or more processors.

The computer unit is provided with a memory 104 holding the digitized signal data obtained from the sensor(s). The computer unit may produce the time series needed for the determination of the two indices. In order to produce the index of nociception the computer unit may further apply the normalization transform to each time series employed and determine the index of nociception based on the normalized signal values. For this purpose, the memory unit 104 may store the transform(s) to be used, the patient-specific and/or group-specific parameter values needed for parameterized transforms, and/or the group-specific input arrays of the histogram transforms to be used. For producing the index of hypnosis, the computer unit may further calculate at least one measure of the complexity of the EEG signal data.

The computer unit may further act as a controlling entity controlling the administration of the drug(s) from a delivery system 107 delivering anesthetic drugs to the patient. Alternatively, as is shown in the example of FIG. 10, the computer unit may supply the time series containing the consecutive value pairs of the two indices to another computer unit or microprocessor 105, which then acts as the controlling entity controlling the drug delivery system. The said controlling entity is provided with a memory 106 storing the control data employed for the administration, such as pharmacokinetic and the pharmacodynamic models, and the indices obtained. The computer units involved are typically provided with dedicated user input devices and monitors. In the embodiment of FIG. 10, the state of the patient may be displayed either through the monitor(s) of the computer unit 103 determining the indices or through the monitor(s) of the computer unit 105 acting as the controlling entity.

Thus, one computer unit or processor may perform the steps of the invention, but the processing of the data may also be distributed among different processors (servers) within a network, such as a hospital LAN (local area network). The apparatus of the invention may thus be implemented as a compact measurement unit or as a distributed system.

Although many of the above embodiments concern closed loop drug administration systems, the system of the invention may also be used in open loop systems where the anesthesiologist controls the administration of the drugs based on the measured state of the patient. If the embodiments of FIGS. 8 to 10 are such open loop systems, the controlling entity, i.e. control unit 81 or computer unit 105, does not control the anesthetic delivery system but may only display the state of the patient through the indicator unit. The control unit may further give recommendations to the anesthesiologist, who then supplies controlling commands through the user input device of the controlling entity. The controlling entity may thus act as in the closed loop system, but instead of controlling the drug administration it may just inform the anesthesiologist of the anesthetic state of the patient and/or give recommendations for the drug administration. In other words, in one embodiment of an open loop system the controlling entity may only indicate the state of patient to the anesthesiologist, who then performs the administration of the drugs based on her or his own expert knowledge. In an embodiment like this, in which the apparatus of the invention only indicates the anesthetic state of the patient, the patient state determination unit may supply the index values directly to the indicator unit. In other embodiments of an open loop system, the system may give various information and/or recommendations to the anesthesiologist, thereby acting as a decision-support tool for the anesthesiologist. The information may include, for example, various displacement information indicative of the displacement of the patient state from the desired state. Although it is preferable to indicate the measured state of the patient graphically in the N-dimensional space/plot defined by the N indices (N=2, 3, . . . ) through a suitable indicator device, such as a graphical display unit, it is also possible that the user is given textual information only.

Although the anesthetic state of the patient may be indicated in various ways, it is important that the displays presented to the anesthesiologist are as informative and descriptive as possible. This is discussed in the following assuming that the anesthetic state is determined by the index of hypnosis and the index of nociception.

Figure 11:
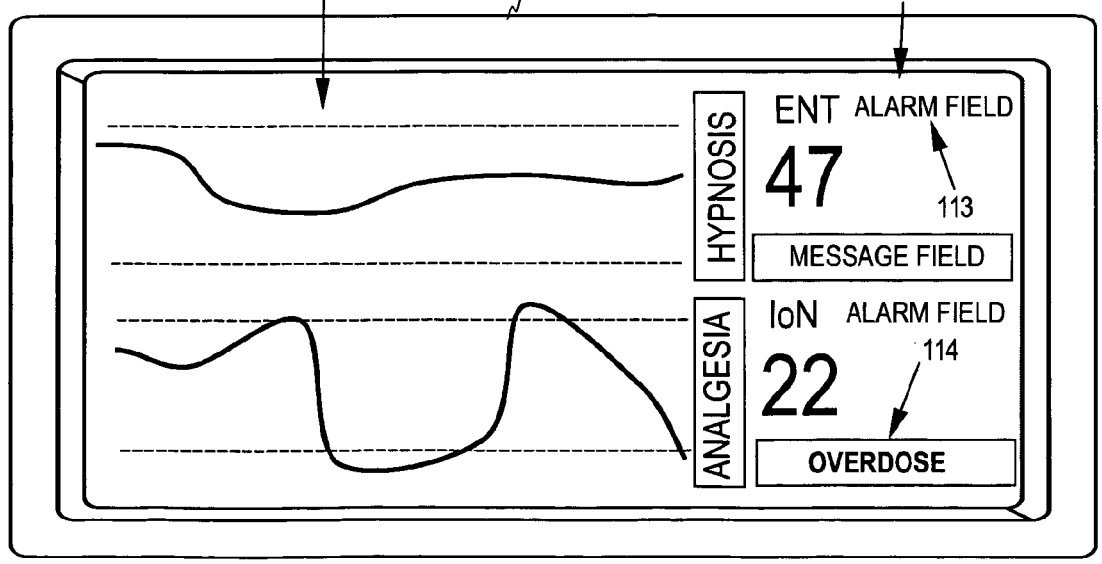
FIGS. 11 to 15 illustrate various mechanisms for presenting the anesthetic state of the patient to the anesthesiologist.

In one embodiment of the apparatus, the monitor displaying the state of the patient is provided with a curve field, in which the indices and their trends are shown as curves, and a numeric field in which numeric information related to the curves is presented. FIG. 11 illustrates such a display or indicator unit 85. The left part of the screen comprises a curve field 111 and the right part a numeric field 112. In this embodiment, the curve field shows an upper curve representing the values of the index of hypnosis and a lower curve representing the values of the index of nociception measured during a preceding time period of a certain length, such as 30 minutes. The horizontal dashed lines in the curve field indicate the upper and lower limits of the permissible value range for both indices. The numeric field shows the current values of the indices and it may further include other information, such as the values of other parameters not shown in the curve field. The screen may further be provided with an alarm field 113 for displaying alarms and a message field 114 for displaying information related to the measurement. As is shown in the figure, each index may have a dedicated alarm and message field. In the example of FIG. 11, the message field of the index of nociception indicates an overdose, since the current value of the said index is below the lower limit of the permissible value range.

Figure 12:
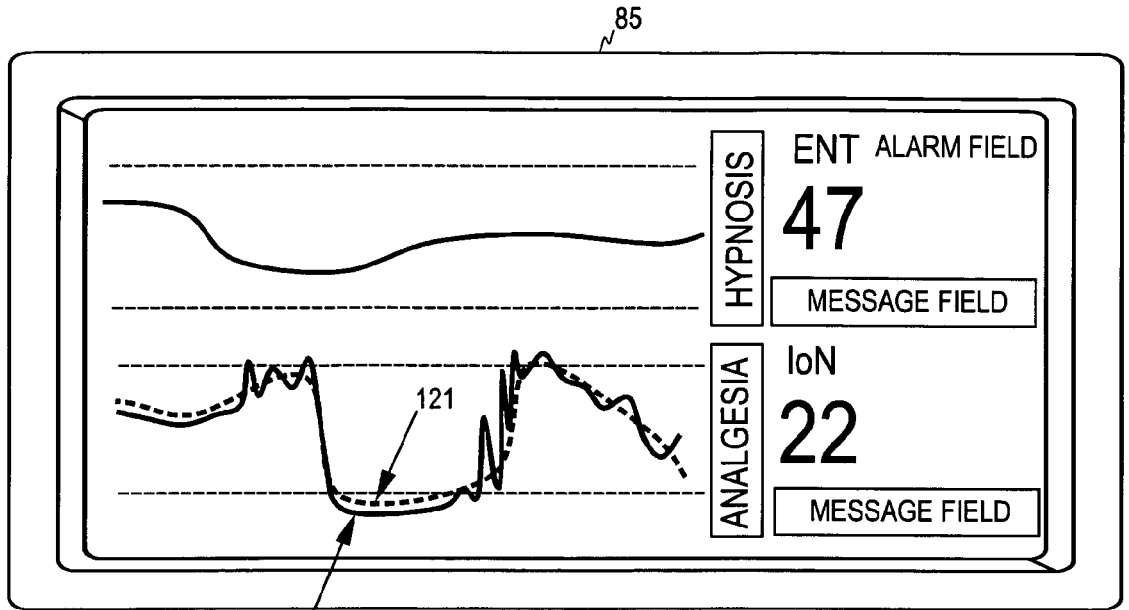

FIG. 12 illustrates a display unit 85 that indicates two curves for the index of nociception. The said curves may be obtained from the same signal data by using two different averaging periods for obtaining the index values or from different signal data characterizing for instance the anesthetic state and the responsiveness of the patient to noxious stimuli For one value of a first curve 121, several index values may therefore be obtained for the second curve 122. In this way, one curve may be employed to show the general trend in the index of nociception (a state index of nociception), while another curve may be employed to show the quick changes in the index (a response index of nociception).

Figure 13:
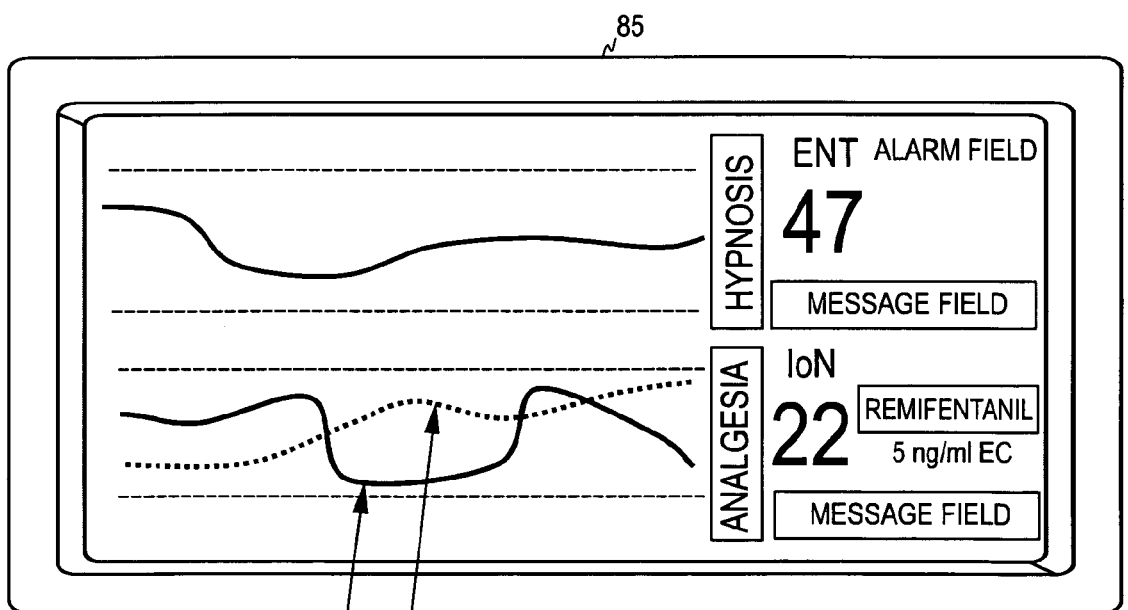

A curve showing the drug concentration may also be displayed together with the curve representing the index. FIG. 13 shows an example, in which a curve 132 representing the analgesic concentration is displayed together with a curve 131 representing the index of nociception. The concentration may be evaluated by means of the PK/PD models. As shown in the figure, the analgesic and its current concentration may also be displayed in the numeric field and/or in the message field. Instead of, or in addition to, the concentration, the display unit may also show the cumulative amount administered to the patient.

Figure 14:
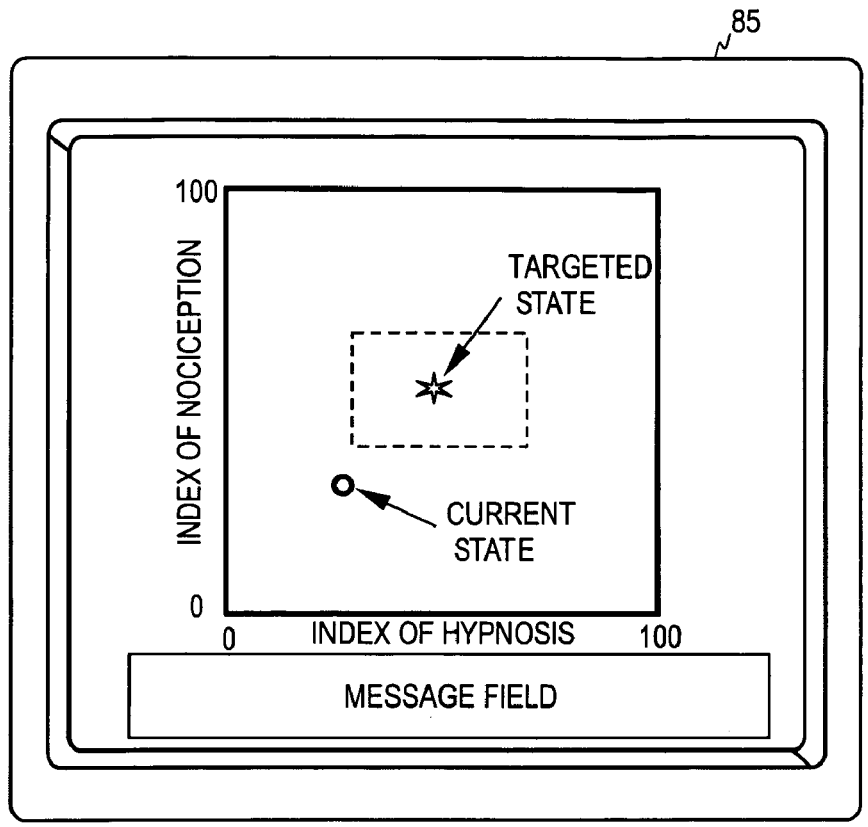

FIG. 14 illustrates a display mode corresponding to the control mechanism illustrated in FIG. 2. In this mode, the displacement of the current state of the patient from the targeted state is indicative the adequacy of the hypnotic and analgesic medication.

Figure 15:
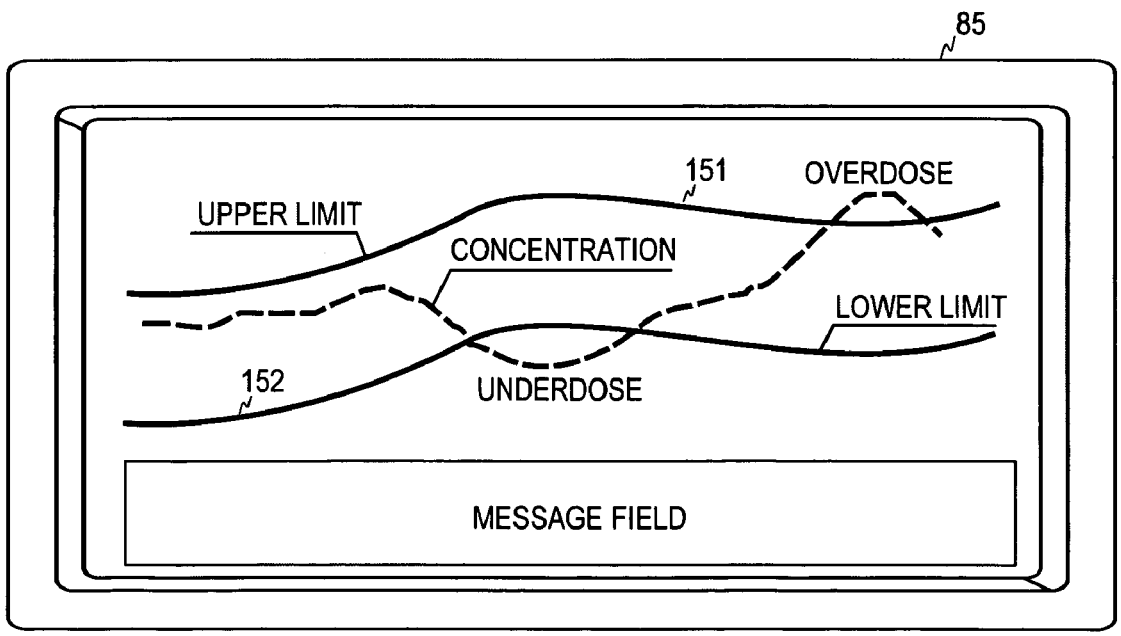

FIG. 15 illustrates an embodiment in which the drug concentration is displayed together with the recommended upper and lower limits for the said concentration. However, in this embodiment the recommended upper and lower limits 151 and 152 of the drug concentration, such as the analgesic concentration, are controlled based on the corresponding index, such as the index of nociception. If the index is too high (underdose), both limits for the recommended drug range shift up for a new, higher, infusion target and if the index is too low (overdose), both limits shift down.

More than one of the above-described display modes may also be used in the same apparatus or measuring arrangement by using several display units with different display modes or by using several display modes in one display unit. For example, the display mode may change when a predetermined event occurs. Furthermore, different colors, visual effects, and/or audio signals may be used in each display mode to call the attention of the nursing staff.

A conventional measurement apparatus may also be upgraded to enable the apparatus to determine the anesthetic state in the above-described manner based on the signal data that the apparatus measures from the patient. Such an upgrade may be implemented by delivering to the measurement apparatus a software module that enables the apparatus to determine the two diagnostic indices in the above-described manner. The software module may be delivered, for example, on a data carrier, such as a CD or a memory card. The software module, which is provided with an interface to the memory storing the signal data measured by the measurement apparatus, may be provided with any of the above-described normalization transforms for the calculation of the index of nociception. It is also possible that a measurement apparatus in which the level of hypnosis is determined is upgraded by adding the determination of the index of nociception.

Although the invention was described above with reference to the examples shown in the appended drawings, it is obvious that the invention is not limited to these, but may be modified by those skilled in the art without departing from the scope and spirit of the invention.

The invention claimed is:

1. A method for determining the anesthetic state of a patient, the method comprising the steps of:
   establishing, using a computer unit, a first index value indicating the current anesthetic state within a predetermined first value range for a first diagnostic index that is indicative of the hypnotic level in the patient;
   establishing, using the computer unit, a second index value for the current anesthetic state in a predetermined second value range for a second diagnostic index that is indicative of the level of analgesia in the patient; and
   utilizing the computer unit to employ the first and second index values to indicate the anesthetic state of the patient, wherein the first and second index values are indicated to the user through an indicator unit by displaying at least two trend curves, each trend curve representing the values of a corresponding diagnostic index during a preceding time period of a certain length.

2. An apparatus for determining the anesthetic state of a patient, the apparatus comprising:
   first means for establishing, a first index value for the current anesthetic state of the patient in a predetermined first value range for a first diagnostic index that is indicative of the hypnotic level of the patient and a second index value for the current anesthetic state of the patient in a predetermined second value range for a second diagnostic index that is indicative of the level of analgesia in the patient;
   second means for employing the first and second index values to indicate the anesthetic state of the patient; and
   an indicator unit for indicating the at least two index values to a user, wherein the indicator unit is configured to display at least two trend curves, each trend curve representing the values of a corresponding diagnostic index during a preceding time period of a certain length.

3. A method for determining the anesthetic state of a patient, the method comprising the steps of:
   establishing, using a computer unit, a first index value indicating the current anesthetic state within a predetermined first value range for a first diagnostic index that is indicative of the hypnotic level in the patient;
   establishing, using the computer unit, a second index value for the current anesthetic state in a predetermined second value range for a second diagnostic index that is indicative of the level of analgesia in the patient, wherein the establishing step comprises the sub-steps of:
   acquiring a first measurement signal containing physiological data indicative from the patient;
   applying a first normalization transform to the first measurement signal, the first normalization transform being dependent on the distribution of previous signal data of said first measurement signal, whereby a first normalized measurement signal having a predetermined value range is obtained;
   forming a normalized index proportional to the first normalized measurement signal;
   employing the normalized index as the second diagnostic index; and
   utilizing the computer unit to employ the first and second index values to indicate the anesthetic state of the patient.

4. A method according to claim 3, wherein the employing step includes the sub-steps of:
   determining a location corresponding to the first and second index values in a space defined by said first and second diagnostic indices; and
   employing the location as the indicator of the anesthetic state of the subject.

5. A method according to claim 4, wherein the employing step includes a sub-step of indicating the location through an indicator unit to a user.

6. A method according to claim 5, wherein the indicating sub-step further includes indicating at least one predetermined reference point in said space, the at least one reference point representing a targeted anesthetic state of the patient.

7. A method according to claim 4, wherein the employing step includes a sub-step of deriving at least one displacement measure indicative of the displacement of said location from at least one predetermined reference point in said space.

8. A method according to claim 7, wherein the at least one predetermined reference point comprises a desired location defined by desired value ranges of the first and second diagnostic indices.

9. A method according to claim 7, wherein the at least one predetermined reference point comprises a single reference point defined by predetermined reference values of the first and second diagnostic indices.

10. A method according to claim 7, further comprising a step of controlling administration of at least one drug to the patient, wherein the at least one drug belongs to a group of drugs including at least one analgesic drug and at least one hypnotic drug, the controlling step being performed based on the at least one displacement measure.

11. A method according to claim 7, wherein the employing step further includes determining, based on the at least one displacement measure, a first measure indicative of the difference in the level of analgesia between said location and the at least one predetermined reference point and a second measure indicative of the difference in the level of hypnosis between said location and the at least one predetermined reference point.

12. A method according to claim 11, further comprising a step of selecting at least one drug to be administered based on said first and second measures.

13. A method according to claim 12, wherein the selecting step includes employing a pharmacokinetic model.

14. A method according to claim 12, wherein the selecting step includes employing a pharmacodynamic model.

15. A method according to claim 3, wherein the employing step includes a sub-step of indicating the first and second index values through an indicator unit to a user.

16. A method according to claim 3, further comprising a step of controlling administration of at least one drug to the patient, wherein the at least one drug belongs to a group of drugs including at least one analgesic drug and at least one hypnotic drug.

17. A method according to claim 3, wherein the step of establishing the first index value comprises the sub-steps of:
obtaining EEG signal data from the patient;
deriving a measure of the complexity of the EEG signal data; and
employing said measure as the first index value within the predetermined first value range for the first diagnostic index.

18. A method according to claim 17, wherein the deriving sub-step includes determining an entropy of the EEG signal data.

19. A method according to claim 3, wherein the forming sub-step includes employing the first normalized signal directly as the normalized index.

20. A method according to claim 3, further comprising the steps of
determining at least one patient-specific value for at least one predetermined parameter of the first measurement signal; and
substituting the at least one patient-specific value for at least one parameter in a predetermined parameterized transform to obtain the first normalization transform.

21. A method according to claim 3, wherein the applying sub-step includes applying a histogram transform to the first measurement signal.

22. A method according to claim 20, wherein the acquiring sub-step includes deriving the first measurement signal from a plethysmographic signal measured from the patient.

23. A method according to claim 20, wherein the acquiring sub-step includes deriving the first measurement signal from a blood pressure signal measured from the subject.

24. A method according to claim 3, wherein the establishing step includes establishing values for three diagnostic indices, wherein a third diagnostic index is indicative of the level of neuromuscular blockade in the patient.

25. A method according to claim 3, further comprising a step of determining, based on the second diagnostic index, at least one reference value serving as an instruction for administering a drug to the subject.

26. A method according to claim 3, further comprising a step of determining, based on the first diagnostic index, at least one reference value serving as an instruction for administering a drug to the subject.

27. The method of claim 3 further comprising the step of:
controlling, using the computer unit, administration of at least one drug to the patient based on the first index value and the second index value, wherein the at least one drug belongs to a group of drugs including at least one analgesic drug and at least one hypnotic drug.

28. An apparatus for determining the anesthetic state of a patient, the apparatus comprising:
first means for establishing a first index value for the current anesthetic state of the patient in a predetermined first value range for a first diagnostic index that is indicative of the hypnotic level of the patient and a second index value for the current anesthetic state of the patient in a predetermined second value range for a second diagnostic index that is indicative of the level of analgesia in the patient, wherein the first means comprises;
means for acquiring a first measurement signal containing physiological data indicative of the cardiovascular function of the patient;
first transform means for applying a first normalization transform to the first measurement signal, the first normalization transform being dependent on the distribution of previous signal data of said first measurement signal, whereby a first normalized measurement signal having a predetermined value range is obtained;
means for forming an index proportional to the first normalized measurement signal, said index serving as the second diagnostic index; and
second means for employing the first and second index values to indicate the anesthetic state of the patient.

29. An apparatus according to claim 28, wherein the second means are configured to determine a location corresponding to the first and second index values in a space defined by said first and second diagnostic indices.

30. An apparatus according to claim 29, wherein the second means include displacement determination means for deriving at least one displacement measure indicative of the displacement of said location from at least one predetermined reference point in said space.

31. An apparatus according to claim 29, further comprising an indicator unit for indicating the location to a user.

32. An apparatus according to claim 31, wherein the indicator unit is configured to indicate at least one predetermined reference point in said space, the at least one reference point representing a targeted anesthetic state of the patient.

33. An apparatus according to claim 28, further comprising drug delivery means for administering at least one drug to the patient, wherein the at least one drug belongs to a group including at least one analgesic drug and at least one hypnotic drug.

34. An apparatus according to claim 33, further comprising control means for controlling the drug delivery means, the control means being operably connected to the displacement determination means.

35. An apparatus according to claim 34, wherein the control means are configured to derive at least one displacement measure indicative of the displacement of said location from at least one predetermined reference point in said space.

36. An apparatus according to claim 35, wherein the control means are configured to determine, based on the at least one displacement measure, a first measure indicative of the difference in the level of analgesia between said location and the at least one predetermined reference point and a second measure indicative of the difference in the level of hypnosis between said location and the at least one predetermined reference point.

37. An apparatus according to claim 28, wherein the first means comprise:
- means for obtaining EEG signal data from the patient; and
- calculation means for deriving a measure of the complexity of the EEG signal data, said measure serving as the first diagnostic index.

38. An apparatus according to claim 37, wherein the calculation means are configured to calculate an entropy of the EEG signal data.

39. An apparatus according to claim 28, further comprising:
- measurement means for determining at least one patient-specific value for at least one predetermined parameter of the first measurement signal; and
- means for substituting the at least one patient-specific value for at least one parameter in a predetermined parameterized transform to obtain the first normalization transform.

40. An apparatus according to claim 28, wherein the first transform means are configured to apply a histogram transform to the first measurement signal.

41. An apparatus according to claim 28, further comprising an indicator unit for indicating the at least two index values to a user.

42. A system for controlling the anesthetic state of a patient, the system comprising:
- means for establishing a first index value for the current anesthetic state in a predetermined first value range for a first diagnostic index that is indicative of the hypnotic level of the patient and a second index value for the current anesthetic state in a predetermined second value range for a second diagnostic index that is indicative of the level of analgesia in the patient, wherein the means comprises;
- means for acquiring a first measurement signal containing physiological data indicative of the cardiovascular function of the patient;
- first transform means for applying a first normalization transform to the first measurement signal, the first normalization transform being dependent on the distribution of previous signal data of said first measurement signal, whereby a first normalized measurement signal having a predetermined value range is obtained;
- means for forming an index proportional to the first normalized measurement signal, said index serving as the second diagnostic index; and
- drug delivery means for administering at least one drug to the patient, wherein the at least one drug belongs to a group of drugs including at least one analgesic drug and at least one hypnotic drug; and
- control means for controlling the drug delivery means based on the first index value and the second index value.

* * * * *